(12) United States Patent
Griffiths et al.

(10) Patent No.: US 7,470,429 B2
(45) Date of Patent: *Dec. 30, 2008

(54) METHODS AND COMPOSITIONS FOR INCREASING THE TARGET-SPECIFIC TOXICITY OF A CHEMOTHERAPY DRUG

(75) Inventors: Gary L. Griffiths, Morristown, NJ (US); Hans J. Hansen, Slidell, LA (US)

(73) Assignee: Immunomedics, Inc., Morris Plains, NJ (US)

( * ) Notice: Subject to any disclaimer, the term of this patent is extended or adjusted under 35 U.S.C. 154(b) by 1423 days.

This patent is subject to a terminal disclaimer.

(21) Appl. No.: 10/066,782

(22) Filed: Feb. 6, 2002

(65) Prior Publication Data

US 2002/0114808 A1 Aug. 22, 2002

Related U.S. Application Data

(62) Division of application No. 09/399,221, filed on Sep. 17, 1999, now Pat. No. 6,361,774.

(60) Provisional application No. 60/101,039, filed on Sep. 18, 1998.

(51) Int. Cl.
*A61K 39/00* (2006.01)
(52) U.S. Cl. .................................................. 424/178.1
(58) Field of Classification Search .............. 424/178.1, 424/9.1, 179.1, 181.1; 530/391.1
See application file for complete search history.

(56) References Cited

U.S. PATENT DOCUMENTS

| | | | |
|---|---|---|---|
| 3,927,193 A | 12/1975 | Hansen et al. | |
| 4,036,945 A | 7/1977 | Haber | |
| 4,331,647 A | 5/1982 | Goldenberg | |
| 4,348,376 A | 9/1982 | Goldenberg | |
| 4,361,544 A | 11/1982 | Goldenberg | |
| 4,444,744 A | 4/1984 | Goldenberg | |
| 4,460,459 A | 7/1984 | Shaw et al. | |
| 4,460,561 A | 7/1984 | Goldenberg | |
| 4,468,457 A | 8/1984 | Goldenberg et al. | |
| 4,735,210 A | 4/1988 | Goldenberg | |
| 5,256,395 A * | 10/1993 | Barbet et al. | 424/1.57 |
| 5,851,527 A | 12/1998 | Hansen | |
| 6,264,917 B1 * | 7/2001 | Klaveness et al. | 424/9.52 |
| 6,312,694 B1 * | 11/2001 | Thorpe et al. | 424/178.1 |
| 6,962,702 B2 * | 11/2005 | Hansen et al. | 424/136.1 |
| 7,074,405 B1 * | 7/2006 | Hansen et al. | 424/136.1 |

FOREIGN PATENT DOCUMENTS

| | | |
|---|---|---|
| EP | 0 501 215 A2 | 2/1992 |
| WO | 91/09134 | 6/1991 |
| WO | WO 9108770 A1 * | 6/1991 |
| WO | 96/20011 | 7/1996 |
| WO | WO 9640245 A1 * | 12/1996 |
| WO | 97/41898 | 11/1997 |
| WO | 99/42593 | 8/1999 |
| WO | 99/66951 | 12/1999 |

OTHER PUBLICATIONS

[Fundamental Immunology 212 (William E. Paul, M.D. ed., 3rd ed. 1993)].*
Trail et al., "Cure of Xenografted Human Carcinomas by BR96-Doxorubicin Immunoconjugates", Science, 1993, pp. 212-215, vol. 261.
Trail et al., "Effect of Linker Variation on the Stability, Potency, and Efficacy of Carcinomareactive BR64-Doxorubicin Immunoconjugates", Cancer Res., 1997, pp. 100-105, vol. 57.
Arcamone, "Properties of Antitumor Anthracyclines and New Developments in Their Application: Cain Memorial Award Lecture", Cancer Res., 1985, p. 5995, vol. 45.
Potter et al., "Isolation and Partial Characterization of a cDNA Encoding a Rabbit Liver Carboxylesterase That Activates the Prodrug Irinotecan (CPT-11)", Cancer Res., 1998, pp. 2646-2651, vol. 58.
Potter et al., "Cellular Localization Domains of a Rabbit and Human Carboxylesterase: Influence on Irinotecan (CPT-11) Metabolism by the Rabbit Enzyme", Cancer Res., 1998, pp. 3627-3632, vol. 58.
Wang et al., "Specific Activation of Glucuronide Prodrugs by Antibody-Targeted Enzyme Conjugates for Cancer Therapy", Cancer Res., 1992, pp. 4484-4491, vol. 52.
Bakina et al., "Intensely Cytotoxic Anthracycline Prodrugs: Glucuronides", J. Med Chem., 1997, pp. 4013-4018, vol. 40.
Schmidt et al., "Glucuronide Prodrugs of Hydroxy Compounds For Antibody Directed Enzyme Prodrug Therapy (Adept) A Phenol Nitrogen Mustard Carbamate", Bioorg. Med Chem. Lett., 1997, pp. 1071-1076, vol. 7.
Gupta et al., "Pharmacokinetic Modulation of Irinotecan and Metabolites by Cyclosporin A", Cancer Res., 1996, pp. 1309-1314, vol. 56.

(Continued)

*Primary Examiner*—Brandon J Fetterolf
(74) *Attorney, Agent, or Firm*—Richard A. Nakashima

(57) ABSTRACT

A method for increasing the target-specific toxicity of a drug is effected by pretargeting an enzyme to a mammalian target site, and then administering a cytotoxic drug known to act at the target site, or a prodrug form thereof which is converted to the drug in situ, which drug is also detoxified to form an intermediate of lower toxicity using said mammal's ordinary metabolic processes, whereby the detoxified intermediate is reconverted to its more toxic form by the pretargeted enzyme and thus has enhanced cytotoxicity at the target site. Further enhancement can be achieved by pretargeting an enzyme which converts the prodrug to the cytotoxic drug at the target site. Kits for use with the method also are provided. The method and kits permit lower doses of cytotoxic agents, maximize target site activity and minimize systemic side effects.

14 Claims, No Drawings

OTHER PUBLICATIONS

Gupta et al., "Modulation of Glucuronidation of SN-38, The Active Metabolite of Irinotecan, by Valproic Acxid and Phenobarbital", Cancer Chemother. Pharmacol., 1997, pp. 440-444, vol. 39.

Melton et al., "Antibody-Directed Enzyme Prodrug Therapy (ADEPT) Review Article", Drugs of the Future 1996, pp. 167-181, vol. 21, No. 2, Barcelona, Spain.

Hay et al., "Antibody-Directed Enzyme Prodrug Therapy (ADEPT)", Drugs of the Future, 1996, pp. 917-931, vol. 21, No. 9.

Takayama et al., "Synthesis of a New Class of Camptothecin Derivatives, The Long-Chain Fatty Acid Esters of 10-Hydroxycampothecin, as a Potent Prodrug Candidate, and Their In Vitro Metabolic Conversion by Carboxylesterases", Bioorganic & Medicinal Chemistry Letters, 1998, pp. 415-418, vol. 8, No. 5, Oxford, Great Britain.

Danks et al., "Comparison of Activation of CPT-11 by Rabbit and Human Carboxylesterases for Use in Enzyme/Prodrug Therapy", Clinical Cancer Research, 1999, pp. 917-924, vol. 5, No. 4.

Leu et al., "Design and Synthesis of Water-Soluble Glucuronide Derivatives of Camptothecin for Cancer Prodrug Monotherapy and Antibody-Directed Enzyme Prodrug Therapy (ADEPT)", Journal of Medicinal Chemistry, 1999, pp. 3623-3628, vol. 42, No. 18.

* cited by examiner

METHODS AND COMPOSITIONS FOR INCREASING THE TARGET-SPECIFIC TOXICITY OF A CHEMOTHERAPY DRUG

CROSS REFERENCE TO RELATED APPLICATIONS

This application is a divisional of U.S. application Ser. No. 09/399,221, filed Sep. 17, 1999, now U.S. Pat. No. 6,361,774, which claims priority from U.S. Provisional Application No. 60/101,039, filed Sep. 18, 1998.

BACKGROUND OF THE INVENTION

The present invention relates to an improved method for increasing the target-specific toxicity of a chemotherapy drug by pretargeting an enzyme to a mammalian target site and administering a cytotoxic drug known to act at the target site, or a prodrug thereof, which drug is also detoxified to form an intermediate of lower toxicity using the mammal's ordinary metabolic processes, whereby the detoxified intermediate is reconverted to its more toxic form by the pretargeted enzyme and thus has enhanced cytotoxicity at the target site. Where a prodrug is used, a further improvement is achieved by targeting a second enzyme to the target site that converts the prodrug to the active drug. Use of versatile bispecific antibodies that can bind more than one kind of enzyme to the target site facilitates efficient enzyme loading and further amplification of the target-specific activity.

It is a continuing aim of chemotherapy to deliver a higher total dose of chemotherapeutic to a tumor target, and/or lower doses to sensitive non-target tissues. Direct attachment of drugs to specific targeting agents such as monoclonal antibodies (MAbs) has a number of drawbacks, including diminishing a drug's potency and changing the pharmacokinetic properties of the MAb for the worse. Despite this, impressive results have been seen in preclinical animal results using conjugates of MAbs and standard chemotherapy drugs such as doxorubicin (Trail et al., *Science* 261:212-215, 1993 & *Cancer Res.*, 57:100-105, 1997). A further problem in translating good animal results to the human situation is that in the latter, tumor target uptake of MAbs is often two to four orders of magnitude lower on a percent injected dose per gram basis.

In part to circumvent the above problems a novel approach was tried whereby an antibody enzyme conjugate was administered, followed sometime later by a precursor of an active drug, i.e. a prodrug. The enzyme localized to target by the tumor-specific antibody would act on the prodrug to release active drug at the target. The method has the advantages of not requiring coupling of drug to MAb, and by virtue of targeted enzyme activity the ability to produce large amounts of drug where it is needed. The latter advantage can overcome the issue of low absolute tumor accretion of MAbs in humans.

In a further modification, a binary system for targeting prodrugs using a bispecific monoclonal antibody (bsMAb) was described by Hansen U.S. Ser. No. 08/445,110 (hereinafter, "Hansen '110"), the disclosure of which is incorporated herein in its entirety by reference. in this system, a bsMAb with an anti-target arm and an anti-enzyme arm is given, followed later by an enzyme, e.g., glucuronidase, which is thus targeted to the disease site. Later still, a prodrug, e.g., a glucuronide prodrug, is administered and the free drug released by the tumor-targeted enzyme. In addition to addressing the issue of low levels of MAb accretion at human tumors, this method has the further advantage of not requiring the coupling of relatively large MAb and enzyme structures, both of whose activities and pharmacokinetic properties can be affected adversely by such conjugations.

One limitation of the bsMAb/prodrug invention as outlined above is the need for a specific antibody directed toward a specific enzyme. Thus, its adoption with different combinations of prodrugs and enzymes would require the preparation of new bsMAbs for each combination.

A need therefore continues to exist for a method for increasing the target-specific toxicity of a chemotherapy drug which is detoxified by normal metabolic processes to form an intermediate of lower toxicity, whereby the detoxified intermediate is reconverted to its more toxic form by the pretargeted enzyme and thus, has enhanced cytotoxicity at the target site.

OBJECTS OF THE INVENTION

One object of the present invention is to enable prodrug systems for enhancing chemotherapy of disease, either by using prodrugs as described previously, or by using commercially available drugs, with the knowledge that their detoxification pathways can be harnessed to improve their therapeutic profiles.

Another object of the present invention is to provide agents useful for treatment of cancer by harnessing a drug's detoxification pathway for improved therapeutic profiles.

A further object of the present invention is to provide multispecific antibodies that can target a variety of enzymes to a target site for significant target-specific amplification of a drug.

Other objects of the present invention will become more readily apparent to those of ordinary skill in the art in light of the following discussion.

SUMMARY OF THE INVENTION

These and other objects of the invention are achieved by providing a method for increasing the target-specific toxicity of a drug, comprising:

(1) pretargeting an enzyme to a mammalian target site; and (2) administering a cytotoxic drug known to act at the target site, or a prodrug form thereof which is converted to the drug in situ, which drug is also detoxified to form an intermediate of lower toxicity using said mammal's ordinary metabolic processes, whereby the detoxified intermediate is reconverted to its more toxic form by the pretargeted enzyme and, thus, has enhanced cytotoxicity at the target site.

The foregoing method is further enhanced by also localizing at the target site an enzyme that converts the prodrug to the active drug.

The invention also provides kits for use in practicing the foregoing method.

DETAILED DISCUSSION

The prior art discloses the attachment of therapeutic or diagnostic agents directly to an antibody, or to a carrier attached to an antibody. Some of the problems associated with conjugating an agent to the antibody include crosslinking, loss of immunoreactivity, immunogenicity, insufficient loading of the agent on the antibody and inadequate deposition of the agent at the target site. The present invention overcomes these problems by pretargeting an enzyme to a target site and then administering a cytotoxic drug, or a prodrug form converted to its cytotoxic form, which is detoxified by ordinary metabolic processes and then reconverted to the toxic form by the pretargeted enzyme, resulting in a more concentrated cytotoxicity at the target site.

The enzyme pretargeting can be accomplished by at least three different methods, each of which is described in detail in Hansen '110. The first method is to directly bind an enzyme to an antibody that selectively binds to at least one antigen present at the target site. The enzyme is thereby localized at the target site.

The second method of pretargeting an enzyme to a target site is through a bispecific antibody or antibody fragment (bsMAb), with at least one binding site specific to an antigen at a target site and at least one other binding site specific to an enzyme. The enzyme can be injected in an amount and by a route which enables a sufficient amount of the enzyme to reach the localized antibody and bind to it to form the antibody-enzyme complex in situ.

In a third alternative, a mammal can be given a bsMAb, one arm of which specifically binds to a target site antigen, e.g., a tumor-associated antigen (TAA) and a second arm of which specifically binds to a low MW hapten, e.g., diethylenetriaminepentaacetic acid (DTPA) or one of its metal complexes. The low MW hapten is in turn chemically bound to the enzyme to be used in the invention. The bsMAb can be an IgG with different functionalities (prepared from quadroma) an IgG-IgG cross-linked bsMAb, or Fab'-Fab', Fab'-F(ab')$_2$, F(ab')$_2$-Fab', F(ab')$_2$-F(ab')$_2$, IgG-Fab', IgG-F(ab')$_2$bsMAbs or bispecific scFvs. All of these agents can be murine, chimeric, humanized or human in origin. Humanized or human antibodies are preferred. The bsMAb is administered and allowed to accrete to its maximum at the target. An enzyme conjugated to the low MW hapten recognized by the second arm of the bsMAb is then administered, whereby the enzyme-hapten conjugate is localized at the target site. Since the recognition is dependent only on the low MW hapten, any enzyme can be used within the scope of the invention. Indeed, a major strength of the approach is that it can be adopted for use with any enzyme-drug pair. Thus, using the bsMAb against DTPA as an example, facile substitution of DTPA onto any enzyme will allow use of an anti-tumor x anti-DTPA bsMAb with any enzyme-drug combination. MAbs have been raised to numerous low MW haptens including DTPA, biotin, p-nitrophenyl-, and fluorescein isothiocyanate groups. Such MAbs can be of various isotypes and isoforms and can be tested and used within the invention when the corresponding hapten is enzyme-linked.

A further significant advantage of this method is that the substitution ratio of the recognition hapten attached to the enzyme can be varied at will. Manipulation of this ratio allows for design of agents with optimum recognition, enzyme activity and pharmacokinetic properties. Another advantage is that the substitution position of the recognition hapten on the enzyme can also be altered at will. Substitution sites such as protein lysyl amino groups, cysteinyl thiol groups and aspartyl/glutamyl carboxylate residues can be used by application of well-known linkage chemistries. Should the enzyme in question possess carbohydrate residues, it too can be used as a chemical attachment site in various well-known ways. The method and degree of hapten substitution onto an enzyme can therefore be chosen to minimize impact on enzymatic activity, an advantage not always possible when directly conjugating enzymes to MAbs or relying of MAb recognition of undefined enzyme epitopes.

Optionally, at this time a primary targeting agent clearing composition can be given. This can be, for instance, a secondary antibody reactive with some part of the targeting molecule, i.e., the antibody-enzyme conjugate or the bsMAb, to remove it from circulation. The secondary MAb can be intact or a fragment, mono- or multi-valent and may be further substituted with agents to enhance circulatory clearance such as galactosyl residues. In the latter instance, multiple galactose substitution directs serum-formed complexes of Mab-enzyme conjugate or bsMAb and secondary MAb to receptors on liver hepatocytes. The clearing agent can also be a high MW protein-bearing haptens recognized by one of the arms of the bsMAb. For instance, if the non-tumor-targeting arm of the bsMAb is directed toward DTPA, a conjugate of comprising human serum albumin and DTPA, optionally further substituted with galactose residues, can be used as a bsMAb clearing agent. Finally, an entirely separate clearing mechanism can be envisaged. The bsMAb can be further substituted with a hapten (e.g. biotin). Once tumor uptake is maximized, a clearing dose of avidin is given. The latter is rapidly sequestered in the liver, and will remove remaining, non-targeted, biotin-bsMAb from circulation. The clearing mechanism is described here as being given before the enzyme-hapten injection, although it can also be given afterwards.

More preferably, a clearing agent is administered to remove non-targeted enzyme/hapten or enzyme/Mab conjugates from circulation prior to administration of said drug or prodrug. When the enzyme is conjugated to a hapten, the clearing agent can be an antibody that binds the hapten. When the enzyme is conjugated to a Mab, the clearing agent can be an anti-idiotypic antibody or anti-idiotypic antibody fragment which is directed to the paratope of the Mab. Clearance of enzyme/hapten or enzyme/Mab conjugates is more effective than clearance of bsMAb, since it limits residual enzyme activity in serum. High residual serum enzyme levels are a limiting factor in the success of targeted immunotherapy.

After the enzyme is pretargeted to the target site, a cytotoxic drug is injected, which is known to act at the target site, or a prodrug form thereof which is converted to the drug in situ. The drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site, in effect recycling the drug.

In another aspect of the invention, a second enzyme that accelerates conversion of a prodrug into its cytotoxic drug product is also localized at the target site. This can be effected by any of the foregoing three mechanisms for enzyme localization. It is especially convenient to use a bsMAb whose second arm binds a hapten, and to conjugate the same hapten to each of the two different enzymes. After localization of the bsMAb at the target site, and optional clearance of non-targeted bsMAb, both enzyme conjugates are administered, in appropriate proportions and order, thereby loading the target with both enzymes. When the prodrug reaches the target site, it will be transformed by the enzyme into a product comprising the therapeutic agent. The enzyme can transform many molecules of prodrug to liberate many molecules of drug, which will accrete at the target site. Thus, the enzyme maximizes site-specific generation of the drug from its prodrug form and thereby minimizes systemic side effects. Further amplification of the site-specific activity of the drug is achieved by the second enzyme which converts a naturally detoxified form the drug, e.g., a glucuronide, which is circulating in the bloodstream and which will eventually be excreted, and-reconverts it at the target site to its cytotoxic form.

Unless otherwise noted, use of the term "antibody" herein will be understood to include antibody fragments and thus to be equivalent to the term "antibody/fragment" which is used interchangeably therefor in this discussion. Antibodies can be whole immunoglobulin of any class, e.g., IgG, IgM, IgA, IgD, IgE, or hybrid antibodies with dual or multiple antigen or epitope specificities, or fragments, e.g., F(ab')2, F(ab)2, Fab[1], Fab and the like, including hybrid fragments.

Antibodies include antiserum preparations, preferably affinity-purified, having a high inuunoreactivity, e.g., a binding constant of at least about 107 l/mole, preferably at least about 109 l/mole, a high immunospecificity, e.g., at least about 40%, preferably at least about 60%, more preferably about 70-95%, and a low cross-reactivity with other tissue antigens, e.g., not more than about 30%, preferably not more than about 15% and more preferably not more than about 5%. The antiserum can be affinity purified by conventional procedures, e.g., by binding antigen to a chromatographic column packing, e.g., Sephadex, passing the antiserum through the column, thereby retaining specific antibodies and separating out other immunoglobulins and contaminants, and then recovering purified antibodies by elution with a chaotropic agent, optionally followed by further purification.

Monoclonal antibodies (Mabs) are also suitable for use in the present method, and are preferred because of their high specificities. They are readily prepared by what are now considered conventional procedures of immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present method.

Antibody fragments can be made by pepsin or papain digestion of whole immunoglobulins by conventional methods such as those disclosed, inter alia, in U.S. Pat. No. 4,331, 647.

The target sites can be, but are not limited to, cancers, infectious and parasitic lesions, fibrin clots, myocardial infarctions, atherosclerotic plaque, damaged normal cells, noncancerous cells and lymphocyte autoreactive clones.

Many antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444, 744, 4,460,459 and 4,460,561, and in related pending applications U.S. Ser. Nos. 609,607 and 633,999, the disclosures of all of which are incorporated in their entireties herein by reference.

Anti-fibrin antibodies are well known in the art. Antibodies that target myocardial infarctions are disclosed in, e.g., Haber, U.S. Pat. No. 4,036,945, the disclosure of which is incorporated in its entirety herein by reference. Antibodies that target normal tissues or organs are disclosed in, e.g., U.S. Pat. No. 4,735,210, the disclosure of which is incorporated in its entirety herein by reference. Anti-fibrin antibodies are well known in the art, as are antibodies that bind to atherosclerotic plaque and to lymphocyte autoreactive clones.

In general, antibodies can usually be raised to any antigen, using the many conventional techniques now well known in the art. Any targeting antibody to an antigen which is found in sufficient concentration at a site in the body of a mammal which is of therapeutic interest can be used to make the targeting antibody molecule for use in the method of the invention.

Multispecific antibodies include but are not limited to bispecific antibodies. Bispecific antibodies can be made by a variety of conventional methods, e.g., disulfide cleavage and reformation of mixtures of whole IgG or, preferably, F(ab')2 fragments, fusions of more than one clone to form polyomas that produce immunoglobulins having more than one specificity, and by genetic engineering. The bispecific antibodies can bind to one or more epitopes on the enzyme but should not bind to a site that interferes with enzyme activity. Alternatively, the bispecific will have a non-targeting arm which binds specifically to a low MW hapten, e.g., a DPTA chelate or other convenient hapten.

The recycling enzyme used in the present invention must be capable of transforming a detoxified, normally more serum-soluble drug, e.g., a glucuronide, to regenerate the drug. Glucuronidases are well known and are representative of suitable recycling enzymes. Other forms of naturally detoxified drugs, such as sulfated or glycosylated (other than glucuronide) molecules can be regenerated at the target site by corresponding enzymes, e.g., sulfatases, glycosylases, and the like. Mutated or otherwise optimized forms of these enzymes also are suitable for use in the invention. Methods for mutation and optimization of enzymes are well known in the art. It will be appreciated by those of skill in the art that molecules that function as enzymes, e.g., abzymes (catalytic antibodies), and the like, will also be suitable for use in the invention and are included in the generic term "enzyme" as used herein as a term for a catalytic molecule for cleaving a prodrug or a detoxified drug conjugate. Similarly, the prodrug cleaving enzyme also can be a mutated and/or optimized form of a natural enzyme or an enzyme mimic such as an abzyme or a synthetic or semisynthetic catalytic molecule.

The prodrug cleaving enzyme and the prodrug itself can be one of those described in Hansen '110 or any other appropriate enzyme or enzyme mimic or prodrug that functions in the manner described herein for components of the inventive methods or compositions.

The targeting molecule can be labeled with, or conjugated or adapted for conjugation to, a radioisotope or magnetic resonance image enhancing agent, to monitor its clearance from the circulatory system of the mammal and make certain that it has sufficiently localized at the target site, prior to the administration of the drug or prodrug. Alternatively, the targeting molecule can be tagged with a label, e.g., a radiolabel, a fluorescent label or the like, that permits its detection and quantitation in body fluids, e.g., blood and urine, so that targeting and/or clearance can be measured and/or inferred.

Any conventional method of labeling proteins for in vivo use will be generally suitable for labeling the targeting molecule, e.g., those disclosed in Hansen '110 or others well known to the skilled artisan.

The drug or prodrug must be soluble for purposes of administration and transport to the target site and the drug must also be capable of being converted to a detoxified form, e.g., a glucuronide, sulfate or glycoside, by the mammalian body. As used herein, the term "soluble" means soluble in the fluid into which it is administered and by which it is transported to the target site, to a sufficient extent to permit transport of a therapeutically effective amount of the drug or prodrug to such site. Normally, drug administration will be into the bloodstream, by intravenous or intra-arterial infusion, and the drug will need to be soluble in serum and preferably sufficiently hydrophilic to be carried largely by the aqueous phase of serum and diffuse relatively easily through the walls of the blood vessels into interstitial fluid, for cases where such is necessary. Oral forms of a drug or prodrug, or other forms well known in the art, that permit transport of the drug or prodrug to the target site or that permit the prodrug to be converted to a drug which then can be transported to the target site, also will be suitable for use in the invention.

This will be better understood in light of some general examples and some more detailed description of various species.

Certain cytotoxic drugs that are useful for anticancer therapy are relatively insoluble in serum. Some are also quite toxic in unconjugated form and their toxicity is considerably reduced by conversion to prodrugs. Conversion of a relatively poorly soluble drug to a more soluble conjugate, e.g., a glucuronide, an ester of a hydrophilic acid, an amide of a hydrophilic amine, will improve its solubility in the aqueous phase of serum and its ability to pass through venous, arterial or capillary cell walls and reach the interstitial fluid bathing the tumor. Cleavage of the prodrug will deposit the less soluble drug at the target site. Many examples of such prodrug-todrug conversions are disclosed in Hansen '110.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase (Arcamone, Cancer Res., 45:5995, 1985). Other analogues with fewer polar groups would be expected to be more lipophilic and show greater promise for such an approach. Other drugs or toxins with aromatic or alicyclic alcohol, thiol or amine groups would also be candidates for such conjugate formation. These drugs, or other prodrug forms thereof, will be suitable candidates for the site-specific enhancement methods of the present invention.

Prodrug forms such as carrier polymer-loaded molecules also are suitable for use in the present methods. This latter example allows for the use of a multiply substituted prodrug in the prodrug administration step. As an illustration of the adaptations to be used for other drugs, loading with 5-flourouracil (5-FU) can be effected by oxidizing 5-flourouridine at the carbohydrate portion, e.g., using periodate, reacting this intermediate with an aminodextran, and reductively stabilizing the Schiff base adduct. Cycloheximide can be loaded by direct reaction of its cyclohexanone carbonyl with aminodextran amine groups, followed by reductive stabilization, or by reacting its side chain hydroxyl with an excess of a diisothiocyanate linker and reaction of the isothiocyanate derivative with amines on the aminodextran, or by reaction of the imide nitrogen with e.g., a haloacid or haloester, followed by activation of the resultant carboxyl derivative, e.g., with DCC, and condensation with amines on the aminodextran. The loaded aminodextran is stripped of drug by an amidase pretargeted to the target site. If the drug is detoxified as a glucuronide, the glucuronide of the drug can be cleaved by a glucuronidase which also has been pretargeted to the target site to regenerate and recycle the cytotoxic drug.

Another illustration is provided by the antibiotic mitomycin C and its analogues. This molecule has an amine function and a cyclic imine, either of which can be reacted with an alkylating activating group, e.g., succinimidyloxy iodoacetate or sulfosuccinimidyloxy (4-iodoacetyl) aminobezoate (sulfo-SIAB), the resulting intermediate is then used to alkylate amine groups on an aminodextran. Alternatively, carboxyl groups can be introduced using, e.g., succinic anhydride, then activated, e.g., with DCC, and the activated intermediate coupled as before. Again, a target-localized amidase will liberate the drug, some drug molecules will be detoxified to form glucuronides, and targeted glucuronidase will regenerate the drug to amplify its target-specific activity.

The prodrug CPT-11 (irinotecan) is converted in vivo by carboxylesterase to the active metabolite SN-38. One application of the invention, therefore, is to use a bsMAb targeted against a tumor and a hapten (e.g. DTPA) followed by injection of a DTPA-carboxyl esterase conjugate. Once a suitable tumor-to-background localization ratio has been achieved, the CPT11 is given and the tumor-localized carboxylesterase serves to convert CPT-11 to SN-38 at the tumor. Since the active SN-38 is poorly soluble it will remain in the vicinity of the tumor and, since it is being generated in the vicinity of the tumor, it is able to exert an effect on adjacent tumor cells that are negative for the antigen being targeted. These are further advantages of the method. Modified forms of carboxylesterase that can be expressed by cells have been described (Potter et al., *Cancer Res.*, 58:2646-2651 and 3627-3632, 1998), and such designed enzymes are within the scope of the invention.

Etoposide is a widely used cancer drug that is detoxified to a major extent by formation of its glucuronide (Hande et al., *Cancer Res.*, 48: 1829-1834, 1988), and could therefore be used within the scope of the invention. Glucuronide conjugates can be prepared from cytotoxic drugs and be injected as therapeutics for tumors pre-targeted with MAb-glucuronidase conjugates (Wang et al., *Cancer Res.*, 52:4484-4491, 1992). Accordingly, such conjugates can also be used with the bsMAb approach described here. Designed prodrugs based on derivatives of daunomycin and doxorubicin have been described (Bakina et al., *J. Med Chem.*, 40:4013-4018, 1997) for use with carboxylesterases and glucuronidases, and these can be used within the scope of the invention. Some other combinations of prodrugs and enzymes that can be used within the invention are listed. Glucuronide prodrugs of hydroxy derivatives of phenol mustards (Schmidt et al., *Bioorg. Med Chem. Lett.*, 7:1071-1076, 1997) and beta-glucuronidase. Phenol mustards or CPT-11 and carboxypeptidase. Methotrexate-substituted alpha-amino acids and carboxypeptidase A. Beta-lactamase and penicillin or cephalosporin conjugates of drugs such as 6-mercaptopurine and doxorubicin. Alkaline phosphatase and etoposide phosphate.

Many drugs and toxins are known which have a cytotoxic effect on tumor cells or microorganisms that may infect a human and cause a lesion, in addition to the specific illustrations given above. They are to be found in compendia of drugs and toxins, such as the Merck Index and the like. The ability to partially or completely detoxify a drug as a prodrug according to the invention, while it is in circulation, can reduce systemic side effects of the drug and permit its use when systemic administration of the drug would be unacceptable. For example, MTX and cycloheximide often are too toxic when administered systemically. Administration of the drug as a prodrug which is only converted to the toxic form at the target site by a pretargeted enzyme, together with recycling and reactivation of the detoxified drug at the target site by a pretargeted second enzyme, permits use of a significantly reduced dose which is still effective for therapy at the target site while mitigating systemic toxicity.

The clearance characteristics of drugs can be modulated by certain agents, and the use of such modulating agents within the invention form an additional embodiment. For example, CPT-11 clearance properties have been shown to be modulated by administration of cyclosporin A with the latter reducing the level of biliary clearance of SN-38 and its glucuronide (SN-38G) (Gupta et al., *Cancer Res.* 56:1309-1314, 1996). In turn, this raised the plasma concentration of SN-38G. This would allow for greater contact with tumor-targeted DTPA-glucuronidase in the present invention. Gupta et al. also showed a similar effect when using phenobarbitol (Cancer Chemother. Pharmacol., 39:440-444, 1997), and thus, this agent could also be given along with CPT-11 after pre-targeting DTPA-glucuronidase. In the latter article they also showed that pretreatment of rats with valproic acid (an inhibitor of uridine diphosphate glucuronosyl transferase (UDP-GT) inhibited the formation of SN-38G leading to a 270% AUC for SN-38 from subsequently-administered CPT-11. Thus, use of valproic acid, within the scope of the invention when pre-targeting DTPA-carboxylesterase to tumor, will also lead to higher levels of SN-38 at the target.

The reagents are conveniently provided as separate injectible preparations for human therapeutic use. The first injectible preparation contains an effective amount of an antibody or antibody fragment conjugated to an enzyme, in a pharmaceutically acceptable injection vehicle, preferably phosphate-buffered saline (PBS) at physiological pH and concentration. The second injectible preparation contains an effective amount of a soluble substrate conjugated to at least one therapeutic agent, in a pharmaceutically acceptable injection vehicle, generally similar to that used for the first preparation. The injectible preparations preferably will be sterile, especially if they are intended for use in humans.

The reagents also can be conveniently provided in a therapeutic kit for antibody targeting to a target site, using suitable containers. Either a container holds an effective amount of a targeting molecule, such as an antibody, which specifically binds to the target site, conjugated to an enzyme capable of converting a detoxified drug to its more cytotoxic form, or the container has an effective amount of a targeting molecule which specifically binds to the target site and which is conjugated to a moiety which can directly or indirectly bind to an enzyme capable of converting a detoxified drug to its more cytotoxic form and, in a separate container, said enzyme in a form capable of binding directly or indirectly to said moiety. The reagents can be lyophilized for longer shelf stability or provided in the form of solutions, optionally containing conventional preservatives, stabilizers and the like. Other optional components of such kits would normally be containers of buffers, labeling reagents, radioisotopes, paramagnetic compounds, second antibody for enhanced clearance, and conventional syringes, columns, vials and the like.

The method of the invention is normally practiced by parenteral injection. The various types of parenteral injections can be, but are not limited to intracavitary (e.g., intraperitoneal), intravenous, intraarterial, intrapleural, intrathecal, intramuscular, intralymphatic and regional intraarterial, intralesional, subcutaneous, catheter perfusion and the like.

For cancer imaging and/or therapy, intravenous, intraarterial or intrapleural administration is normally used for lung, breast, and leukemic tumors. Intraperitoneal administration is advantageous for ovarian tumors. Intrathecal administration is advantageous for brain tumors and leukemia. Subcutaneous administration is advantageous for Hodgkin's disease, lymphoma and breast carcinoma. Catheter perfusion is useful for metastatic lung, breast or germ cell carcinomas of the liver. Intralesional administration is useful for lung and breast lesions.

The enzyme will generally be administered as an aqueous solution in PBS, preferably a sterile solution, especially if it is for use in humans. Advantageously, dosage units of about 50 micrograms to about 5 mg of the enzyme will be administered, either in a single dose or in divided doses, although smaller or larger doses may be indicated in particular cases. It may be necessary to reduce the dosage and/or use antibodies from other species and/or hypoallergenic antibodies, e.g., fragments or hybrid human or primate antibodies, to reduce patient sensitivity, especially for therapy and especially if repeated administrations are indicated for a therapy course or for additional diagnostic procedures. An indication of the need for such cautionary procedures is an increase in human anti-mouse antibody (HAMA) production, which can be determined using an immunoassay.

It usually takes from about 2 to 14 days and preferably 5 to 14 days for IgG antibody to localize at the target site and substantially clear from the circulatory system of the mammal prior to administration of the drug or prodrug. The corresponding localization and clearance time for F(ab)2 and F(ab$^1$)2 antibody fragments is from about 2 to 7 days and preferably 4 to 7 days, and from about 1 to 3 days and preferably 3 days for Fab and Fab$^1$ antibody fragments. Other antibodies may require different time frames to localize at the target site, and the above time frames may be affected by the presence of the conjugated enzyme. Again, it is noted that labeling the enzyme permits monitoring of localization and clearance.

IgG is normally metabolized in the liver and, to a lesser extent, in the digestive system. F(ab)2 and F(ab$^1$)2 are normally metabolized primarily in the kidney, but can also be metabolized in the liver and the digestive system. Fab and Fab$^1$ are normally metabolized primarily in the kidney, but can also be metabolized in the liver and the digestive system.

Normally, it will be necessary for at least about 0.0001% of the injected dose of antibody-enzyme conjugate to localize at the target site prior to administration of the substrate-agent conjugate. To the extent that a higher targeting efficiency for this conjugate is achieved, this percentage can be greater, and a reduced dosage can be administered.

It follows that an effective amount of an antibody-enzyme conjugate is that amount sufficient to target the conjugate to the antigen at the target site and thereby bind an amount of the enzyme sufficient to transform enough of the glucuronide to its cytotoxic form to result in accretion of an effective therapeutic amount of the drug at the target site.

The drug may be given in doses, and at times, that can be optimized empirically for a particular combination. It may be given as a single injection or infusion, or may be administered in repeat doses. It can most preferably be given from one to two hundred hours after the haptenenzyme is administered, and if given in multiple doses, can most preferably be given at intervals from every hour to every three days. The therapeutic drug will be generally administered as an aqueous solution in PBS. Again, this will be a sterile solution if intended for human use. The drug will be administered after a sufficient time has passed for the enzyme to localized at the target site and substantially clear from the circulatory system of the mammal.

An effective amount of a prodrug is that amount sufficient to deliver an effective amount of the drug to the target site. An effective amount of a therapeutic drug is that amount sufficient to treat the target site.

The therapeutic method of the invention can be accomplished by conjugating an effective therapeutic amount of a radioisotope such as Y-90 or I-131 (which may be used for both localization and therapy depending on the amount injected) or a drug such as adriamycin for cancer or gentamycin for infection, an immunomodulatory substance such as poly-IC, or a biological toxin such as pokeweed mitogen to the substrate, and depositing a therapeutically effective amount of the agent at the target site.

Dosage units of substrate-agent conjugate will depend upon many factors, each of which can be determined in a relatively straightforward manner, so that optimal dosimetry can be effected. It will be helpful, in the initial dosimetric evaluation, to use a radiolabeled substrate-agent conjugate (if the agent is not itself a radioactive isotope) to determine the degree and rate of deposit of the agent at the target site, and the rate of clearance and biodistribution of non-targeted conjugate. Use of a labeled antibody-enzyme conjugate to estimate the amount of enzyme localized at the target site will also aid in dosimetric analysis.

It may be necessary to perform trials for dosimetry, generally using an animal model first, if available, then in a series of patient studies, to optimize the dose of substrate-agent conjugate, as a function of accessibility of the site, mode of administration, turnover number of the enzyme, desired dose of the agent to the site, and rate of clearance of non-targeted conjugate. This will be expected and the techniques for optimization will be within the ordinary skill of the clinician.

Without further elaboration, it is believed that one skilled in the art can, using the preceding description, utilize the present invention to its fullest extent. The following preferred specific embodiments are, therefore, to be construed as merely illustrative, and not a limitation of the remainder of the disclosure in any way whatsoever. In the following examples, all temperatures are set forth uncorrected in degrees Celsius; unless otherwise indicated, all parts and percentages are by weight.

EXAMPLES

Example 1

Preparation of Antibody-enzyme Conjugates (A) A substantially monoconjugated enzyme-antibody preparation is prepared by mildly oxidizing the carbohydrate portion of a humanized anti-lymphoma Fab' having a light chain glycosylation site with periodate, then contacting the oxidized Fab' with a dilute solution of glucuronidase (from bovine liver, Worthingon) to produce an antibody-enzyme conjugate, which is then stabilized by borohydride, in the usual manner. The conjugate can be radiolabeled with I-131, by conventional procedures.

(B)) In a similar fashion to the above Part A, the humanized anti-lymphoma Fab' is conjugated to carboxylesterase.

Example 2

Therapy of Lymphoma

A human patient suffering from lymphoma is infused intravenously with a sterile, pyrogen-free PBS solution containing 5 mg each of the 1-13 1-labeled anti-lymphoma Fab'-glucuronidase and esterase conjugates prepared according to Example 1 hereof. After 3 days, the conjugates are well localized at the target site and substantially cleared from the circulatory system, as determined by gamma scanning.

The patient is then infused intravenously with a sterile, pyrogen-free PBS solution containing 10 mg of epirubicin methyl ester. Subsequent radioimmunodetection shows significant reduction in the lymphoma, compared to a 10 mg dosage of epirubicin prior to targeting with the enzyme conjugates.

Example 3

Preparation of Bispecific Antibody (bsMAb)

An IgG×Fab' bsMAb is made in the following manner. Humanized MIN-14 IgG (antiCEA) is treated with sodium periodate to specifically oxidize heavy chain carbohydrate residues. Formed aldehyde groups are reacted with an excess of the commercially available cross-linking agent MBPH {4-(4-N-maleimidophenyl)butyric acid hydrazide; Pierce Chemical Co., Rockford, Ill.}. Non-reacted MBPH is removed from the modified hMN-14 MAb by size-exclusion chromatography and the hMN-14-(maleimide)$_n$ intermediate is reacted with a small molar excess of the Fab'-SH fragment of the anti-DTPA MAb {termed 734}, generated from its IgG by standard pepsin digestion and thiol reduction. The desired bsMAb IgG×Fab' moiety is separated from unreacted proteins and non-1:1 conjugates by preparative size-exclusion HPLC. Further purification may be effected by affinity chromatography using a solid-phase-bound DTPA affinity column.

Example 4

Preparation of Clearing Agent

Anti-idiotypic MAb to hMN-14, termed W12, is treated over 2 h with a 300-fold molar excess of the imidate from cyanomethyl-2,3,4,6-tetra-O-acetyl-1-thio-β-D-galactopyranoside (CTTG), that is prepared freshly using sodium methoxide. The galactosyl-W12 thus formed is purified by size-exclusion chromatography. Fluorometric analysis of the product in comparison with unmodified MAb shows that approximately 80% of the MAbs lysine residues are substituted with a galactose residue.

Example 5

Preparation of Enzyme-hapten Conjugates

The enzyme carboxylesterase (CE) is treated with a five-fold molar excess of DTPA-dianhydride (Sigma Chemical Co., St. Louis, Mich.). After stirring for one hour, the DTPA-CE is purified from free DTPA and aggregated enzyme by preparative size-exclusion HPLC. Approximately 1-2 DTPA units are appended per enzyme. Similarly, glucuronidase is conjugated to DTPA using the dianhydride.

Example 6

Tumor Therapy

A patient with colorectal cancer is given an injection of the bsMAb comprised of an IgGhMN-14 cross-linked with an anti-DTPA Fab' fragment, prepared according to Example 3. After 48 h to allow for maximum accretion in tumors, an amount of galactose-W12, prepared according to Example 4, sufficient to clear nearly all non-target-bound MN-14-IgG ×734-Fab' from the circulation is administered. This amount is between 5 and 15 times the amount of primary bsMAb remaining in circulation at the time-point specified. Three hours after administration of the galactose-W12, a tumor-saturating amount of a mixture of the DTPA-CE and DTPA-glucuronide conjugates is given, and allowed to clear circulation and normal tissues. Another three hours later, a standard chemotherapy dose of CPT-11 is administered to the patient, generating free SN-38 specifically at the tumor target sites, regenerating free SN-38 at the target sites from the glucuronide, and destroying the tumors.

Example 7

Tumor Therapy

A patient with colorectal cancer is given an injection of the bsMAb as in Example 6. After 48 h to allow for maximum accretion in tumors, an excess amount of same mixture of the DTPA-CE and DTPA-glucuronidase conjugates as in Example 6 is given. Three hours later an amount of galactose-W12 sufficient to clear nearly all non-target-bound M/N-14-IgG ×734-Fab'-DTPA-enzymes from the circulation is administered. This amount is between 5 and 15 times the amount of primary bsMAb complexes remaining in circulation at the time-point specified. Another three hours later, a standard chemotherapy dose of CPT-11 is administered to the patient, generating free SN-38 specifically at the tumor target sites, recycling SN-38 glucuronide at the target site, and destroying said tumors.

It will be appreciated by the skilled artisan that the foregoing examples are merely illustrative and that modifications and variants may be readily envisaged, all of which are part of the present invention.

What is claimed is:

1. A method for increasing the target-specific toxicity of a chemotherapeutic agent, comprising:
    a) pretargeting an enzyme to a mammalian target site, wherein said pretargeting comprises (i) administering a bispecific antibody or binding fragment thereof, wherein one arm of the bispecific antibody is targeted against a target site antigen and a second arm is targeted against a low molecular weight hapten that is conjugated to said enzyme and (ii) administering a low molecular weight hapten that is conjugated to said enzyme; and
    b) administering a cytotoxic chemotherapeutic agent known to act at the target site, or a prodrug form thereof which is converted to the chemotherapeutic agent in situ, which chemotherapeutic agent is also detoxified to form an intermediate of lower toxicity using said mammal's ordinary metabolic processes, whereby the detoxified intermediate is reconverted to its more toxic form by the pretargeted enzyme and thus has enhanced cytotoxicity at the target site, wherein said hapten is DTPA or a DTPA chelate.

2. The method of claim 1, wherein said enzyme is a glucuronidase.

3. The method of claim 1, wherein said mammal is a human.

4. The method of claim 1, wherein said bispecific antibody or binding fragment thereof comprises murine, chimeric or humanized antibodies or binding fragments thereof.

5. A method for increasing the target-specific toxicity of a chemotherapeutic agent, comprising:
    a) pretargeting an enzyme to a mammalian target site, wherein said pretargeting comprises (i) administering a bispecific antibody or binding fragment thereof, wherein one arm of the bispecific antibody is targeted against a target site antigen and a second arm is targeted against a low molecular weight hapten that is conjugated to said enzyme and (ii) administering a low molecular weight hapten that is conjugated to said enzyme; and
    b) administering a cytotoxic chemotherapeutic agent known to act at the target site, or a prodrug form thereof which is converted to the chemotherapeutic agent in situ, which chemotherapeutic agent is also detoxified to form an intermediate of lower toxicity using said mammal's ordinary metabolic processes, whereby the detoxified intermediate is reconverted to its more toxic form by the pretargeted enzyme and thus has enhanced cytotoxicity at the target site, wherein said prodrug is the cancer chemotherapy agent CPT-11, and said detoxified intermediate is SN-38-glucuronide.

6. The method of claim 5, further comprising pretargeting an esterase to said target site that cleaves CPT-11 to SN-38.

7. A method for increasing the target-specific toxicity of a chemotherapeutic agent, comprising:
    a) pretargeting an enzyme to a mammalian target site, wherein said pretargeting comprises (i) administering a bispecific antibody or binding fragment thereof, wherein one arm of the bispecific antibody is targeted against a target site antigen and a second arm is targeted against a low molecular weight hapten that is conjugated to said enzyme and (ii) administering a low molecular weight hapten that is conjugated to said enzyme; and
    b) administering a cytotoxic chemotherapeutic agent known to act at the target site, or a prodrug form thereof which is converted to the chemotherapeutic agent in situ, which chemotherapeutic agent is also detoxified to form an intermediate of lower toxicity using said mammal's ordinary metabolic processes, whereby the detoxified intermediate is reconverted to its more toxic form by the pretargeted enzyme and thus has enhanced cytotoxicity at the target site, wherein a second enzyme, which can convert the prodrug to the chemotherapeutic agent, also is conjugated to said hapten, and wherein the second enzyme also is pretargeted to said target site.

8. The method of claim 7, wherein said hapten is DTPA or a DTPA chelate.

9. The method of claim 1, wherein additionally, a clearing agent is administered to remove non-targeted pretargeting molecules and/or enzymes from said mammal's circulation prior to administration of said chemotherapeutic agent or prodrug.

10. The method of claim 9, wherein said clearing agent is an anti-MAb antibody or an anti-idiotype antibody.

11. A method for increasing the target-specific toxicity of a chemotherapeutic agent, comprising:
    a) pretargeting an enzyme to a mammalian target site, wherein said pretargeting comprises(i) administering a bispecific antibody or binding fragment thereof, wherein one arm of the bispecific antibody is targeted against a target site antigen and a second arm is targeted against a low molecular weight hapten that is conjugated to said enzyme; and (ii) administering a low molecular weight hapten that is conjugated to said enzyme; and
    b) administering a cytotoxic chemotherapeutic agent known to act at the target site, or a prodrug form thereof which is converted to the chemotherapeutic agent in situ, which chemotherapeutic agent is also detoxified to form an intermediate of lower toxicity using said mammal's ordinary metabolic processes, whereby the detoxified intermediate is reconverted to its more toxic form by the pretargeted enzyme and thus has enhanced cytotoxicity at the target site, wherein, a clearing agent is administered to remove non-targeted pretargeting molecules and/or enzymes from said mammal's circulation prior to administration of said chemotherapeutic agent or prodrug, and said clearing agent is an antibody that binds said hapten.

12. The method of claim 9, wherein said enzyme is conjugated to a Mab and said clearing agent is an anti-idiotypic antibody or anti-idiotypic antibody binding fragment thereof which is specific for the paratope of said Mab.

13. The method of claim 1, wherein said enzyme is selected from the group consisting of a glycosylase other than glucuronidase, a sulfatase, an esterase or an amidase.

14. The method of claim 1, wherein said antibody binding fragment thereof comprises an Feb, Fab', F(ab)2, F(ab')2 or scFv fragment.

* * * * *